(12) United States Patent
Norton et al.

(10) Patent No.: US 8,765,070 B2
(45) Date of Patent: Jul. 1, 2014

(54) SYSTEM AND METHOD FOR REJECTING HEAT FROM EQUIPMENT VIA ENDOTHERMIC ISOMERIZATION

(75) Inventors: Daniel G. Norton, Niskayuna, NY (US); Robert J. Perry, Niskayuna, NY (US); Edward H. Allen, Bethesda, MD (US); Paul B. Glaser, Albany, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 1286 days.

(21) Appl. No.: 12/564,804

(22) Filed: Sep. 22, 2009

(65) Prior Publication Data
US 2011/0067839 A1 Mar. 24, 2011

(51) Int. Cl.
*B01J 19/00* (2006.01)
*B01J 8/00* (2006.01)
*B64D 37/34* (2006.01)
*B64D 33/08* (2006.01)
*B01J 8/02* (2006.01)
*F02C 7/12* (2006.01)

(52) U.S. Cl.
CPC .............. *B64D 37/34* (2013.01); *B64D 33/08* (2013.01); *B01J 8/0285* (2013.01); *F02C 7/12* (2013.01); *B01J 2208/065* (2013.01); *B01J 2208/00132* (2013.01)
USPC ........... 422/201; 422/198; 422/200; 422/205; 422/206; 422/657; 422/658; 422/659

(58) Field of Classification Search
CPC ...... B01J 8/02; B01J 8/0285; B01J 2208/065; B01J 2208/00132; B64D 37/02; B64D 37/06; B64D 37/34; B64D 33/08; B64D 2013/0633; B64D 2013/0614; F02C 7/12

USPC ......... 422/657, 658, 659, 198, 200, 201, 205, 422/206
See application file for complete search history.

(56) References Cited

U.S. PATENT DOCUMENTS

| | | | | |
|---|---|---|---|---|
| 3,032,599 | A | * 5/1962 | Bailey et al. | .................. 585/730 |
| 3,132,110 | A | 5/1964 | Hansford | |
| 3,215,753 | A | 11/1965 | Bloch et al. | |
| 3,357,916 | A | * 12/1967 | Smith | ...................... 208/120.05 |

(Continued)

OTHER PUBLICATIONS

Resofszki et al., "Electron spectroscopy of sulfated zirconia, its activity in n-hexane conversion and possible reasons of its deactivation," Science Direct, 2003, pp. 71-81, Applied Catalysis A: General, Elsevier.

(Continued)

*Primary Examiner* — Lessanework Seifu
(74) *Attorney, Agent, or Firm* — Reising Ethington P.C.

(57) ABSTRACT

A system for rejecting heat from equipment using endothermic isomerization. includes a heat exchanger configured to receive an elevated-temperature process fluid and an isomerization compound capable of endothermic isomerization. When the system is in operation, heat from the elevated temperature process fluid is transferred to the isomerization compound and the isomerization compound endothermically isomerizes to a higher energy state form. A vehicle includes an engine and a body. The body houses a catalytic heat exchanger having an output in fluid communication with the engine, a pump for urging an isomerization compound into the heat exchanger, and a heat sink controller for controlling the pump. A method for rejecting heat from equipment using endothermic isomerization includes providing a compound capable of endothermic isomerization and transferring heat from a process fluid to the compound, such that the compound endothermically isomerizes to a higher energy level isomer.

7 Claims, 6 Drawing Sheets

(56) References Cited

U.S. PATENT DOCUMENTS

| | | | |
|---|---|---|---|
| 3,587,618 A * | 6/1971 | Kenyon | 137/87.06 |
| 4,086,284 A | 4/1978 | Schneider et al. | |
| 4,116,880 A * | 9/1978 | Olah | 502/168 |
| 4,406,821 A | 9/1983 | Farcasiu | |
| 4,508,618 A | 4/1985 | Olah | |
| 5,149,018 A | 9/1992 | Clark | |
| 5,151,171 A | 9/1992 | Spadaccini et al. | |
| 5,161,365 A * | 11/1992 | Wright | 60/780 |
| 5,176,814 A | 1/1993 | Spadaccini et al. | |
| 5,232,672 A | 8/1993 | Spadaccini et al. | |
| 5,255,505 A * | 10/1993 | Cloyd et al. | 60/806 |
| 5,267,608 A | 12/1993 | Coffinberry | |
| 5,392,595 A * | 2/1995 | Glickstein et al. | 60/780 |
| 6,180,555 B1 | 1/2001 | Szabo et al. | |
| 6,846,402 B2 | 1/2005 | Hemighaus et al. | |
| 7,320,748 B2 | 1/2008 | Hemighaus et al. | |
| 2004/0013606 A1* | 1/2004 | Tonkovich et al. | 423/652 |
| 2007/0178029 A1* | 8/2007 | Goebbel et al. | 422/227 |
| 2010/0275607 A1* | 11/2010 | Allen | 60/772 |

OTHER PUBLICATIONS

Matsuda et al., "Selective skeletal isomerization of alkanes over partially reduced MoO3," Catalysis Surveys from Asia, Dec. 2004, pp. 275-283, vol. 8, No. 4, Springer Science Business Media, Inc.

Matsuda et al., "Reduction of MoO3 to Porous Molybdenum Oxides and Its Catalytic Properties for Alkane Isomerization," Journal of the Japan Petroleum Institute, 2007, pp. 229-239, vol. 50, No. 5.

Kuba et al., "Reaction pathways in n-pentane conversion catalyzed by tungstated zirconia: effects of platinum in the catalyst and hydrogen in the feed," Science Direct, 2003, pp. 376-388, Journal of Catalysis, Elsevier.

Xu et al., "A Highly Effective Pt and H3PW12O40 Modified Zirconium Oxide Metal-Acid Bifunctional Catalyst for Skeletal Isomerization: Preparation, Characterization and Catalytic Behavior Study," Catal Lett, Jul. 2008, pp. 340-347, vol. 125, Springer Science Business Media, LLC.

Wang et al., "n-Pentane isomerization over promoted SZ/MCM-41 catalysts," Catalysis Today 97, 2004, pp. 307-313, Science Direct, Elsevier.

Chen et al., "Highly active and stable n-pentane isomerization catalysts without noble metal containing: Al- or Ga-promoted tungstated zirconia," Catalysis Letters, Nov. 2006, pp. 187-193, vol. 111, Nos. 3-4, Springer Science Business Media Inc.

Lopez et al., "n-Pentane Hydroisomerization of Pt Containing HZSM-5, HBEA and SAPO-11," Catal Lett, Mar. 2008, pp. 267-273, vol. 122, Springer Science Business Media LLC.

Ryu et al., "n-Hexane Conversion Catalyzed by Sulfated Zirconia and by Iron- and Manganese-Promoted Sulfated Zirconia: Catalytic Activities and Reaction Network," Ind. Eng. Chem. Res., Mar. 1998, pp. 1786-1792, vol. 37.

Li et al., "Mechanism of butane skeletal isomerization on sulfated zirconia," Journal of Catalyst 232, 2005, pp. 456-466, Science Direct, Elsevier.

Duchet et al., "Mechanism for isomerization of n-hexane over sulfated zirconia: role of hydrogen," Chem. Commun., 1999, pp. 1819-1820.

Rezgui et al., "n-pentane isomerization and disproportionation catalyzed by promoted and unpromoted sulfated zirconia," Catalysis Letters 51, 1998, pp. 229-234, AG, Science Publishers.

Farcasiu et al., "The Kinetics of isomerization of 3-methylpentane catalyzed by triflouromethanesulfonic acid," J. Chem. Soc., Perkin Trans. 2, 1999, pp. 1609-1613.

Volkova et al., "n-Hexane skeletal isomerization over sulfated zirconia catalysts with different Lewis acidity," Chemical Engineering Journal 134, 2007, pp. 106-110, Elsevier.

Fraissard et al., "Isomerization of hexane of PtAu nanoparticles supported on zeolites," Catalyst Today 122, 2007, pp. 338-340, Science Direct, Elsevier.

Duchet et al., "Isomerization of n-Hexane over Sulfated Zirconia: Influence of Hydrogen and Platinum," Journal of Catalyst 198, 2001, pp. 328-337, Academic Press.

Gagea et al., "Isomerization of cyclohexane and hexane over silica-embedded triflate dervative catalysts," Arkivoc (ii), 2002, pp. 46-55, ARKAT USA, Inc.

Farcasiu et al., "Isomerization of hexane by zeolite HZSM-5 The effect of cyclic hydrocarbons," Journal of Molecular Catalysis A: Chemical 161, 2000, pp. 213-221, Elsevier Science.

Karinen et al., "Reaction Equilibrium in the Isomerization of 2,4,4-Trimethyl Pentenes," Ind. Eng. Chem. Res. 40, 2001, pp. 1011-1015.

Santiesteban et al., "The Role of Platinum in Hexane Isomerization over Pt/FeOy/WOx/ZrO2," Journal of Catalyst 202, 2001, pp. 25-33, Academic Press.

Yoshioka et al., "n-Hexane isomerization on Ni-Pt catalysts/supported on HUSY zeolite: The influence from a metal content," Catalysis Today, 2005, pp. 693-698, Elsevier.

Bogdan et al., "Gas-Phase and Supercritical n-Pentane Isomerization on H-Mordenite," Kinetics and Catalysts, 2007, pp. 785-788, vol. 48.

Comelli et al., "Effect of operational conditions during n-hexane isomerization over platinum on tungsten-oxide promoted zirconia," Catalyst Letters 55, 1998, pp. 177-182, Baltzer AG, Science Publishers.

Farcasiu et al., "The Mechanism of Conversion of Saturated Hydrocarbons Catalyzed by Sulfated Metal Oxides: Reaction of Adamantane on Sulfated Zirconia," Journal of Catalysis 158, 1996, pp. 116-127, Academic Press, Inc.

Hamouda et al., "Control Preparation of Sulfated Zirconia by Sol-Gel Process: Impact on Catalytic Performances During n-Hexane Isomerization," Journal of Sol-Gel Science and Technology 19, 2000, pp. 413-416, Kluwer Academic Publishers.

Zarubica et al., "Content of sulfates and their stability—key factors determining the catalytic activity of sulfated zirconia catalysts," J. Serb. Chem. Soc. 72(7), 2007, pp. 679-686.

Lonyi et al., "Hexane Isomerization and Cracking Activity and Intrinsic Acidity of H-Zeolites and Sulfated Zirconia-Titania," J. Phys. Chem. B, 2006, pp. 1711-1721.

Loften, Thomas, "Catalytic isomerization of light alkanes," Norwegian University of Science and Technology, Dec. 2004.

* cited by examiner

SYSTEM AND METHOD FOR REJECTING HEAT FROM EQUIPMENT VIA ENDOTHERMIC ISOMERIZATION

BACKGROUND

1. Field of the Invention

The present invention relates to heat sinks. In particular, the present invention relates to heat sinks for mobile implementations, such as vehicles.

2. Description of Related Art

Equipment in vehicles, such as airborne vehicles, land-based vehicles, space-based vehicles, and other such mobile equipment often generate heat that must be dissipated or rejected. For example, heat produced by an automobile engine is rejected via coolant flowing through the automobile's radiator. In low-speed aircraft, heat is often rejected via the aircraft's skin to the air flowing over the skin. In other implementations, however, rejecting heat is more difficult. For example, air impacting onto a high-speed aircraft often imparts heat into the aircraft's skin due to friction, instead of removing heat from the skin. If rejecting heat from such equipment is difficult or impossible, the equipment will continue to undesirably increase in temperature so long as heat is being generated within the equipment.

One conventional way of rejecting heat produced by equipment in vehicles is to transfer the heat into fuel used to power the equipment. When the fuel is burned, the rejected heat leaves the equipment. Problems, however, exist with such implementations. Firstly, if sufficient heat is rejected into the fuel, the temperature of the fuel may increase to the point where the fuel thermally breaks down. This situation can cause buildups of deposits within the equipment's fuel system, resulting in reduced equipment performance and/or undesired behavior. Secondly, the fuel may come into contact with components, such as gaskets and electronics, of the equipment that have limited tolerance to high temperatures.

There are many ways of rejecting heat from mobile equipment and the like well known in the art, however, considerable shortcomings remain.

DESCRIPTION OF THE DRAWINGS

The novel features believed characteristic of the invention are set forth in the appended claims. However, the invention itself, as well as, a preferred mode of use, and further objectives and advantages thereof, will best be understood by reference to the following detailed description when read in conjunction with the accompanying drawings, in which the leftmost significant digit(s) in the reference numerals denote(s) the first figure in which the respective reference numerals appear, wherein:

Figure 1:
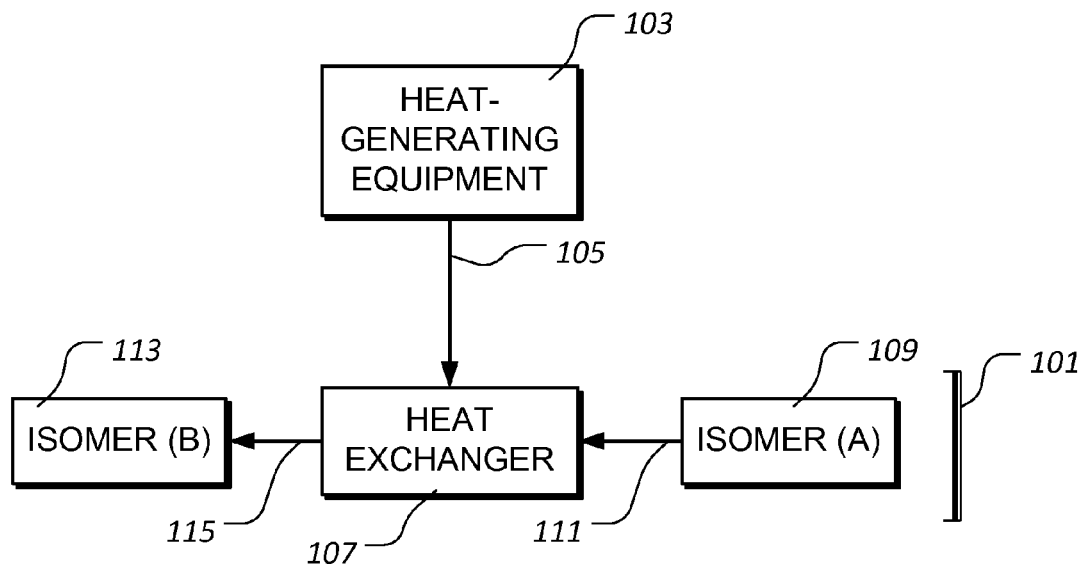
FIG. 1 is a graphical representation of an illustrative embodiment of a system for rejecting heat from heat-generating equipment.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

The present invention represents a system and method for rejecting heat from equipment via endothermic isomerization. FIG. 1 provides a graphical representation of an illustrative embodiment of a system 101 for rejecting heat from a heat-generating equipment 103. In the illustrated embodiment, a process fluid, represented by an arrow 105, is outputted from equipment 103 to a heat exchanger 107. A compound capable of endothermically isomerizing, i.e., "isomer (A)" 109, is inputted to heat exchanger 107, as indicated by an arrow 111. Heat from process fluid 105 is transferred to isomer (A) 109 within heat exchanger 107, thus endothermically isomerizing isomer (A) 109 to "isomer (B)" 113, which is outputted from heat exchanger 107, as indicated by an arrow 115.

The present invention contemplates many compounds that exhibit isomerism. An isomeric compound exists in two or more structural forms; however, the two or more structural forms have the same molecular formula. For a group of isomers, each isomer has a given enthalpy of formation, as a function of temperature and pressure. If, for example, the temperature of the isomer of the compound having the lowest enthalpy of formation is increased, heat will be absorbed by the isomer and at least a portion of the isomer will change form to an isomer of the compound having a higher enthalpy of formation. At a particular temperature and pressure, an isomeric compound will exist at an equilibrium mixture of the one or more isomers of the compound. If, for example, the mixture contains an isomer of the compound that exhibits a lower enthalpy of formation than the equilibrium mixture of the isomers and the temperature of the mixture is increased, the lower enthalpy of formation-isomer will absorb heat and change form to an isomer of the compound having a higher enthalpy of formation.

Figure 2A:
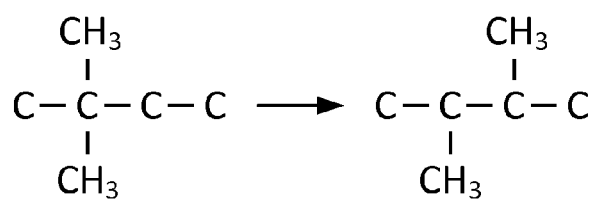
FIGS. 2A-2D depict structural representations of chemical reactions occurring in the isomerization of hexane.
Figure 2B:
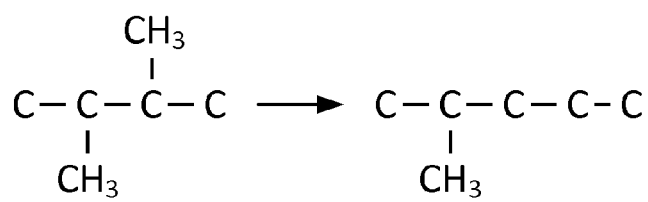
Figure 2C:
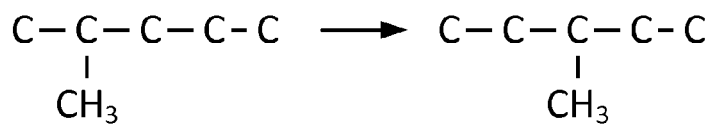
Figure 2D:
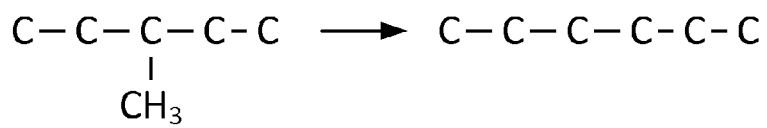

In one exemplary embodiment, the isomeric compound is hexane. All isomeric forms of hexane exhibit the molecular formula $C_6H_{14}$. However, hexane exists as five structurally different isomers: 2,2-dimethylbutane, 2,3-dimethylbutane, 2-methylpentane, 3-methylpentane, and n-hexane, i.e., normal hexane. FIGS. 2A-2D depict the structural changes resulting from the isomerization of 2,2-dimethylbutane to 2,3-dimethylbutane (FIG. 2A); 2,3-dimethylbutane to 2-methylpentane (FIG. 2B); 2-methylpentane to 3-methylpentane (FIG. 2C); and 3-methylpentane to n-hexane (FIG. 2D). The isomers of hexane have the following enthalpies of formation at a temperature of 25° C. and at a pressure of one atmosphere:

| Isomer | Enthalpy of formation (kilojoules per mole) |
|---|---|
| n-hexane | −167.3 |
| 3-methylpentane | −172.4 |
| 2-methylpentane | −174.9 |
| 2,3-dimethylbutane | −177.2 |
| 2,2-dimethylbutane | −185.0 |

Thus, 2,2-dimethylbutane exhibits the lowest heat of formation of the isomers of hexane. Isomerization of 2,2-dimethylbutane to any of the other four isomers of hexane is endothermic. The most endothermic isomerization reaction for hexane is the isomerization of 2,2-dimethylbutane to n-hexane, which would absorb 17.7 kilojoules of heat per mole of hexane. For example, if pure 2,2-dimethylbutane were to react to form pure n-hexane, 205.6 Joules per gram of heat would be absorbed directly as a result of the reaction. However, equilibrium limits the conversion that can be achieved without additional separation.

Figure 3:
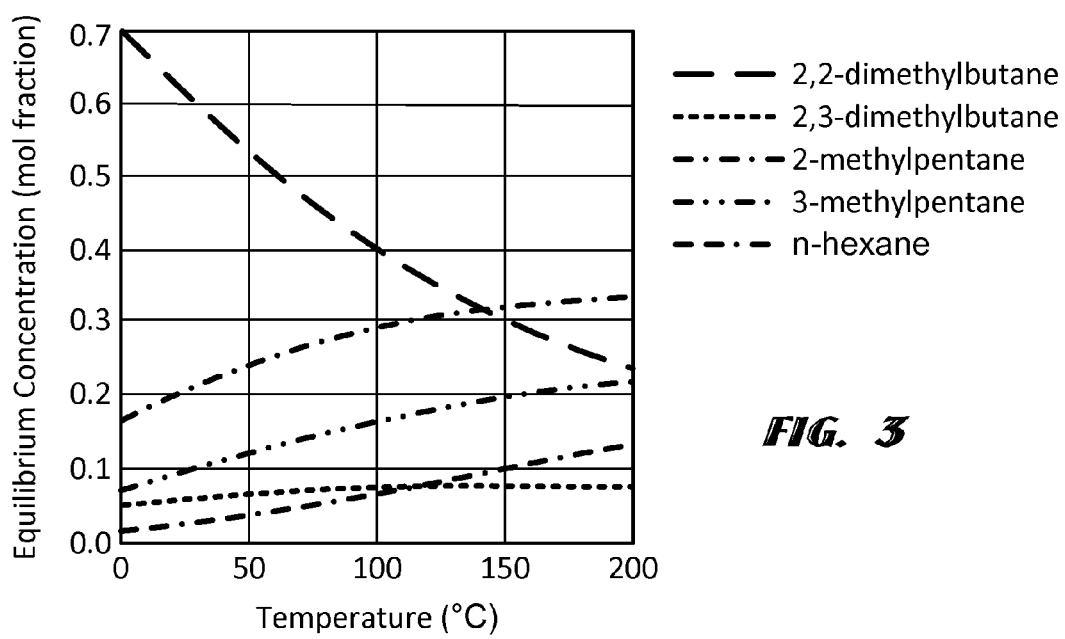
FIG. 3 is a chart depicting exemplary concentrations of the isomers of hexane at various temperatures.
Figure 4:
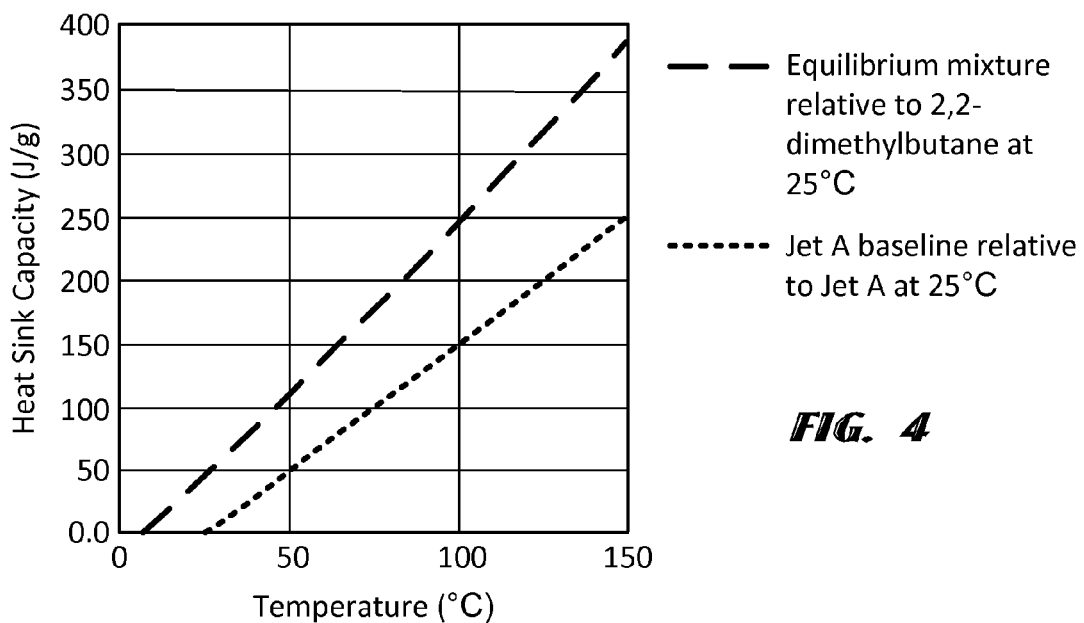
FIG. 4 is a chart depicting exemplary equilibrium heat sink capacity for hexane isomerization and heat sink capacity for baseline Jet A fuel heating at various temperatures.

FIG. 3 depicts exemplary concentrations of the isomers of hexane at various temperatures. For example, at 50° C., the equilibrium mixture contains approximately 53 molecular percent 2,2-dimethylbutane. At 100° C., the equilibrium mixture contains approximately 40 molecular percent 2,2-dimethylbutane. As the temperature increases, the fraction of 2,2-dimethylbutane in the equilibrium mixture decreases and the fraction of n-hexane in the equilibrium mixture increases. Additionally, if the starting mixture is at a first, lower temperature and the final mixture is at a second, elevated temperature, both the heat of isomerization and the heat required to raise the temperature of the mixture can be sunk into the mixture. For example, as shown in FIG. 4, raising the temperature of the mixture from 25° C. to 100° C. can sink about 245 joules of heat per gram of mixture. By comparison, raising the temperature of "Jet A" fuel from 25° C. to 100° C. sinks only about 150 joules of heat per gram of Jet A fuel.

As presented herein, the present invention contemplates compounds other than hexane as isomerization compounds. For example, octane ($C_8H_{18}$), heptane ($C_7H_{16}$), pentane ($C_5H_{12}$) and butane ($C_4H_{10}$) may, in certain embodiments, be used as isomerization compounds.

Figure 5:
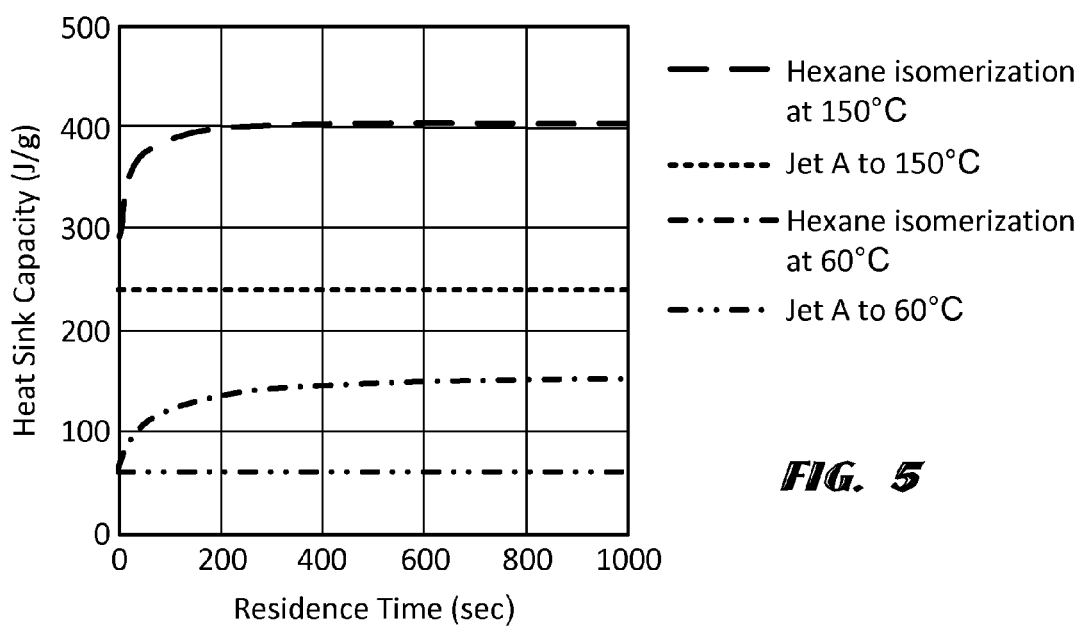
FIG. 5 is a chart depicting exemplary heat sink capacities for various residence times of hexane isomerization at 60° C. and at 150° C. using sulfated zirconia as a catalyst and at a pressure of about 1.5 megapascals in a constantly stirred reactor, as well as exemplary heat sink capacities of Jet A fuel when the temperature thereof is increased to 60° C. and to 150° C.
Figure 6:
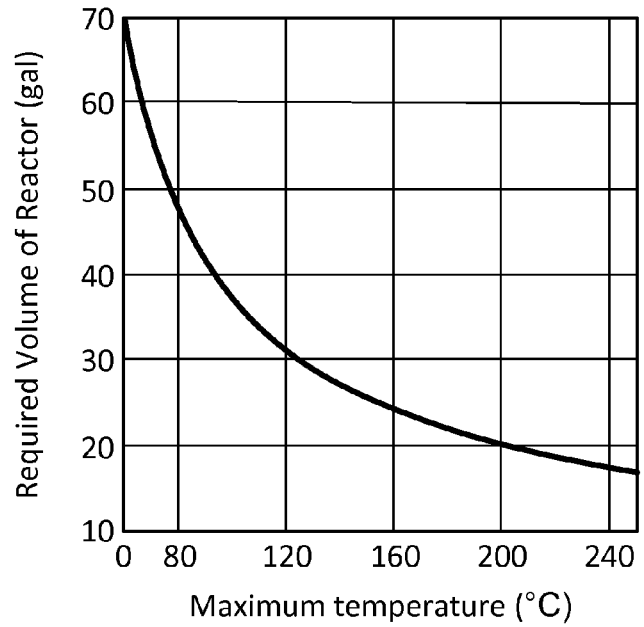
FIG. 6 is a chart depicting exemplary reactor volumes at various temperatures required to achieve 23 kilowatts of power sink at an operating pressure of 1.5 megapascals, assuming a 60 second residence time.

The change from a more endothermic mixture to the equilibrium mixture only provides heat sink capacity, not the rate at which the mixture can sink heat. For example, if a system has a very large sink between a first, more endothermic state and the equilibrium state, but the isomerization reaction rates are slow, the system may be unable to sink the heat at an acceptable rate. Accordingly, in at least such situations, the present invention contemplates the use of a catalyst to increase the isomerization rate. One particular catalyst contemplated by the present invention is sulfated zirconia. FIG. 5 depicts exemplary heat sink capacities for various residence times of hexane isomerization at 60° C. and at 150° C. using sulfated zirconia as a catalyst and at a pressure of about 1.5 megapascals in a constantly stirred reactor, as well as exemplary heat sink capacities of Jet A fuel when the temperature thereof is increased to 60° C. and to 150° C. As kinetics are slower at lower temperatures, longer times are required at lower temperatures to achieve the equilibrium state. For example, at 60° C., about five minutes are required to approach the equilibrium state, whereas at 150° C. only about two minutes are required to approach the equilibrium state. As the temperature increases, the volume of the reactor required to sink a given amount of power decreases, because the residence time drops. FIG. 6 depicts exemplary reactor volumes at various temperatures required to achieve 23 kilowatts of power sink at an operating pressure of 1.5 megapascals, assuming a 60 second residence time. For example, referring to FIG. 6, a reactor volume of about 58 gallons would be required to sink 23 kilowatts of power at an operating temperature of 80° C. and an operating pressure of 1.5 megapascals, assuming a 60 second residence time. At 200° C., however, a reactor volume of only about 20 gallons would be required to sink 23 kilowatts of power at an operating pressure of 1.5 megapascals, assuming a 60 second residence time.

It should be noted that catalysts other than sulfated zirconia are contemplated by the present invention. For example, aluminum trichloride ($AlCl_3$), fluoroantimonic acid (HF—$SbF_5$), or the like may be used as catalysts and, in particular, may be used in systems utilizing hexane isomerization.

Figure 7:
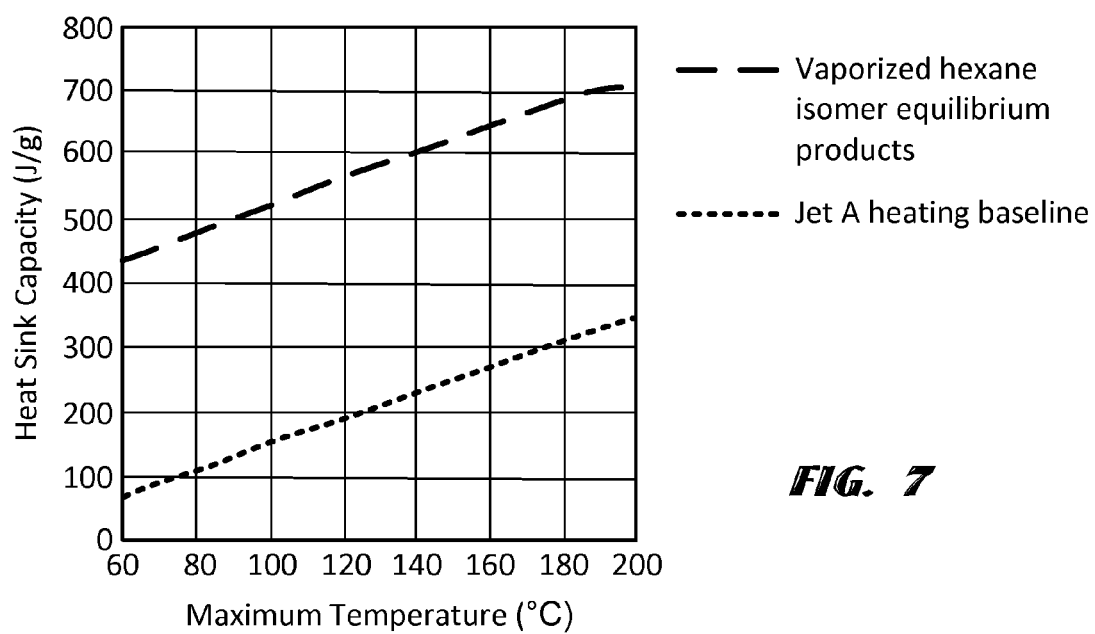
FIG. 7 is a chart depicting heat sink capacity for 2,2-dimethylbutane isomerization with vaporization and baseline Jet A fuel heating at various temperatures.

If either the reactants or the products of isomerization are vaporized during the process, some additional heat can be sunk. In some implementations, the latent heat of vaporization can be a significant heat sink. In the case of hexane isomerization, the products of isomerization vaporize at temperatures within a range of about 50° C. to about 69° C. at atmospheric pressure. Vaporizing the products of isomerization can provide, for example, an additional 300 joules per gram of heat sink capacity, as shown in FIG. 7.

Figure 8:
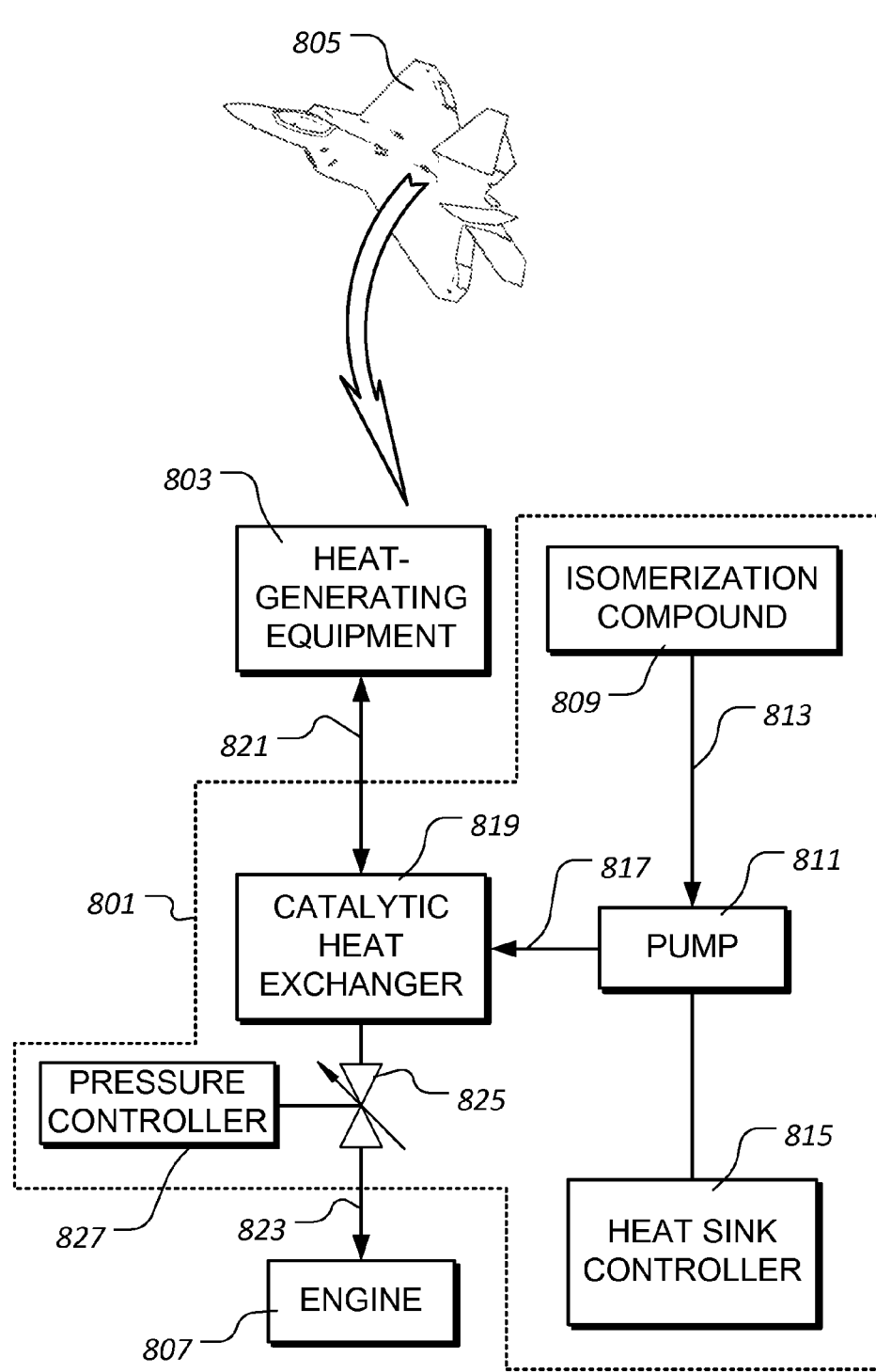
FIG. 8 is a stylized, graphical representation of an illustrative embodiment of a system for rejecting heat generated by heat-generating equipment of a vehicle.

FIG. 8 depicts an illustrative embodiment of a system 801 for rejecting heat generated by heat-generating equipment 803 of a vehicle 805. In the illustrated embodiment, vehicle 805 is an aircraft. System 801 may be applied to many various heat-generating equipments 803. In one embodiment, heat-generating equipment 803 is an engine 807 for propelling vehicle 803; however, the scope of the present invention is not so limited. System 801 comprises a reservoir of an isomerization compound 809 capable of endothermic isomerization, such as the isomerization compounds discussed herein. Isomerization compound 809 is provided to a pump 811, as indicated by an arrow 813. A heat sink controller 815 controls pump 811 to transfer, as indicated by an arrow 817, isomerization compound 809 to a catalytic heat exchanger 819. Process fluid from heat-generating equipment 803 is transferred, as indicated by an arrow 821, to catalytic heat exchanger 819. Heat is transferred from heat-generating equipment 803 to the process fluid. The process fluid is the vehicle by which heat from heat-generating equipment 803 is carried to catalytic heat exchanger 819. In one embodiment, the process fluid is recirculated to heat-generating equipment 803 after being processed by catalytic heat exchanger 819. The present invention contemplates any process fluid, either in a gaseous or liquid state, suitable for a particular implementation of system 801. In catalytic heat exchanger 819, heat from the process fluid is transferred to isomerization compound 809 causing isomerization of compound 809 to a higher energy-level form, e.g., from 2,2-dimethylbutane to 2,3-dimethylbutane if hexane is isomerization compound 809. The endothermically isomerized form of isomerization compound 809, in one embodiment, is then fed, as indicated by an arrow 823, into engine 805 of vehicle 805 as a fuel.

Still referring to FIG. 8, in certain embodiments, system 801 further comprises a valve 825 in fluid communication with catalytic heat exchanger 819. A pressure controller 827 controls valve 825 to maintain a desired pressure within catalytic heat exchanger 819 to, for example, provide a suitable environment for isomerization compound 809 to be vaporized by heat from the process fluid. In embodiments wherein the endothermically isomerized form of isomerization compound 809 is fed as a fuel into engine 805, valve 825 is in fluid communication with both catalytic heat exchanger 819 and engine 805.

Figure 9:
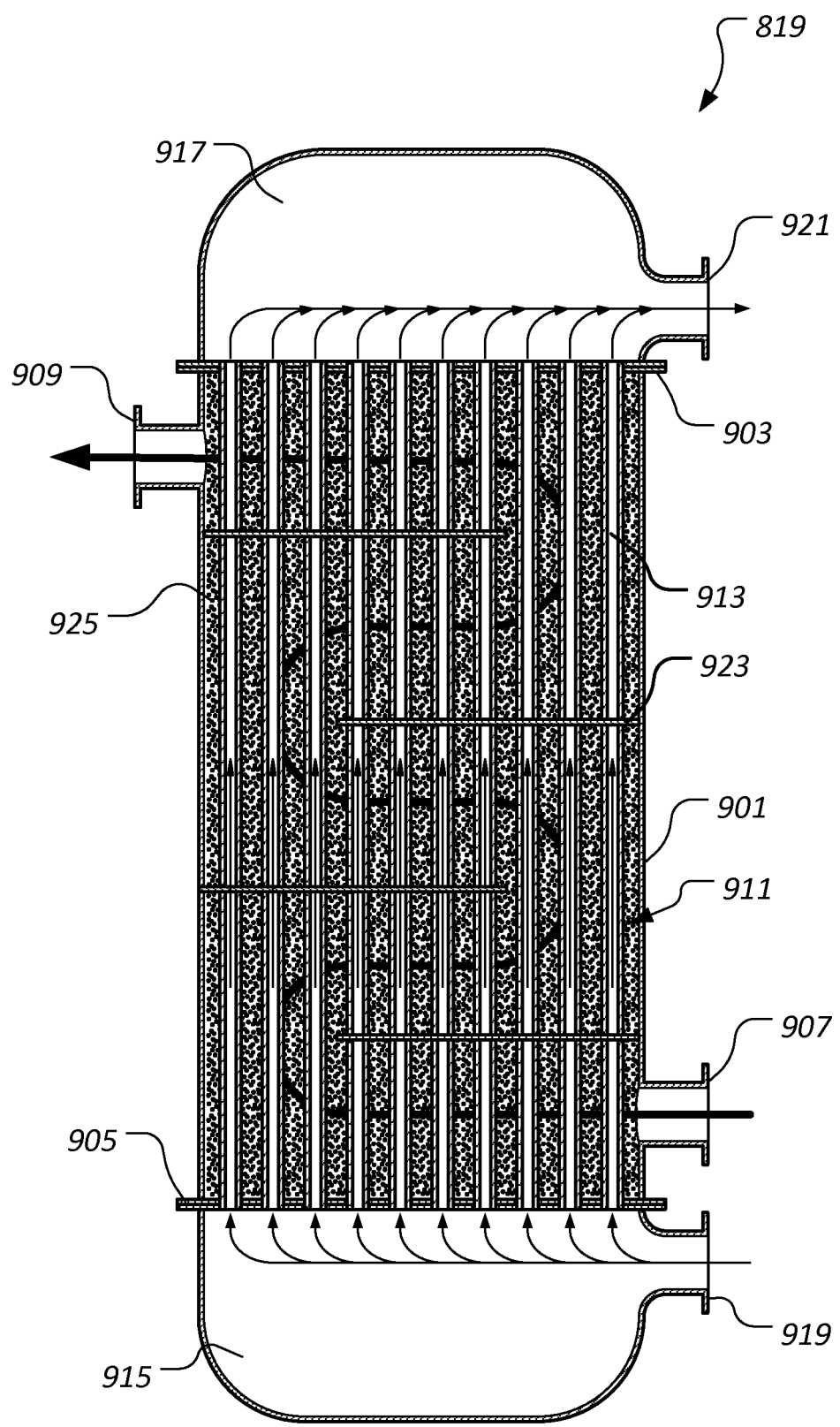
FIG. 9 is a cross-sectional view of an illustrative embodiment of a catalytic heat exchanger of the system shown in FIG. 8.

FIG. 9 depicts an illustrative embodiment of a shell and tube, catalytic heat exchanger 819, although the present invention contemplates other configurations of catalytic heat exchanger 819, such as a "U-tube" catalytic heat exchanger, a "two-pass tube side, straight tube" heat exchanger, or the like. In the illustrated embodiment, catalytic heat exchanger 819 comprises a shell 901 terminated by a first tube sheet 903 and a second tube sheet 905. An inlet 907 and an outlet 909 are in fluid communication with an interior 911 of shell 901, such that interior 911 is substantially closed except for ingress via inlet 907 and egress via outlet 909. In use, inlet 907 is in fluid communication with pump 811 (shown in FIG. 8) and, in certain embodiments, outlet 909 is in fluid communication with valve 825 (shown in FIG. 8) and/or with engine 807 (shown in FIG. 8). A plurality of tubes 913 (only one tube 913 labeled in FIG. 9 for clarity) extend between and through first tube sheet 903 and second tube sheet 905.

Shell 901, with tube sheets 903 and 905 attached thereto, is disposed between an inlet plenum 915 and an outlet plenum 917, which are in fluid communication with the plurality of tubes 913. Inlet plenum 915 defines an inlet 919 and outlet plenum 917 defines an outlet 921. In use, inlet 919 is in fluid communication with heat-generating equipment 803 (shown in FIG. 8) and, in certain embodiments, outlet 921 is also in fluid communication with heat-generating equipment in a closed-loop configuration. Inlet plenum 915 and outlet plenum 917 are affixed to second tube sheet 905 and first tube sheet 903 such that, in use, fluid flowing through the plurality of tubes 913 only communicates into inlet plenum 915 through inlet 919 and communicates into outlet plenum 917 through outlet 921. A plurality of baffles 923 (only one baffle 923 is labeled in FIG. 9 for clarity) extend into interior 911 of shell 901, such that some of the tubes of the plurality of tubes 913 extend through one or more of the plurality of baffles 923. A catalyst 925, such as sulfated zirconia or other catalyst, such as those described herein, is disposed within interior 911 of shell 901 about the plurality of tubes 913 and the plurality of baffles 923.

Still referring to FIG. 9, when in operation, elevated temperature process fluid flows from heat-generating equipment 803 (shown in FIG. 8) through inlet 919, through inlet plenum 915, through the plurality of tubes 913, through outlet plenum 917, and through outlet 921. As discussed herein, the process fluid is routed back to heat-generating equipment 803 in certain embodiments in a closed-loop system. Heat is transferred from the process fluid, through the plurality of tubes 913, into interior 911 of shell 901. Isomerization compound 809 (shown in FIG. 8), in a state capable of endothermically isomerizing, flows from pump 811 (shown in FIG. 8) through shell inlet 907, through interior 911 of shell 901, and through shell outlet 909. While flowing through interior 911 of shell 901, isomerization compound 809 is in the presence of catalyst 925. Heat from the process fluid is transferred into isomerization compound 809, thus endothermically isomerizing isomerization compound 809, e.g., from 2,2-dimethylbutane to 2,3-dimethylbutane if hexane is isomerization compound 809. Thus, heat from the process fluid is absorbed by isomerization compound to raise its temperature and to change its structure from a lower-energy form to a higher-energy form. Isomerized compound 809 may also be vaporized, thus further absorbing heat from the process fluid.

It should be noted that the method of the present invention can be performed at low temperatures, e.g., within a range of about $-25°$ C. to about $200°$ C., and at reasonable pressures, e.g., within a range of about five psia to about 200 psia.

In one aspect, the present invention provides a system for rejecting heat from equipment using endothermic isomerization. The system includes a heat exchanger configured to receive an elevated-temperature process fluid and an isomerization compound capable of endothermic isomerization. When the system is in operation, heat from the elevated temperature process fluid is transferred to the isomerization compound and the isomerization compound endothermically isomerizes to a higher energy state form. In another aspect, the present invention provides a vehicle, including an engine and a body. The body houses a catalytic heat exchanger having an output in fluid communication with the engine, a pump for urging an isomerization compound into the heat exchanger, and a heat sink controller for controlling the pump. In yet another aspect, the present invention provides a method for rejecting heat from equipment using endothermic isomerization. The method includes providing a compound capable of endothermic isomerization and transferring heat from a process fluid to the compound, such that the compound endothermically isomerizes to a higher energy level isomer.

The present invention provides significant advantages, including: (1) allowing a large amount of excess heat to be rejected; (2) avoiding undesirable effects of rejecting heat into conventional fuel; (3) allowing heat to be rejected within a large range of temperatures and pressures; (4) allowing heat to be rejected within low temperature ranges and at reasonable pressures; and (5) using the compound used for heat transfer as a fuel.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below. It is apparent that an invention with significant advantages has been described and illustrated. Although the present invention is shown in a limited number of forms, it is not limited to just these forms, but is amenable to various changes and modifications without departing from the spirit thereof.

What is claimed is:

1. A system for rejecting heat from equipment using endothermic isomerization, comprising:

heat-generating equipment situated on-board an aircraft;

a shell and tube catalytic heat exchanger configured to receive a liquid process fluid and an isomerization compound capable of endothermic isomerization, wherein the liquid process fluid circulates between the heat-generating equipment and the shell and tube catalytic heat exchanger;

wherein, when the system is in operation, the liquid process fluid transfers heat to the isomerization compound within the shell and tube catalytic heat exchanger such that the isomerization compound endothermically isomerizes to a higher energy state form.

2. The system of claim 1, wherein the shell and tube catalytic heat exchanger comprises:

a catalyst comprising one of sulfated zirconia, aluminum trichloride, and fluoroantimonic acid.

3. The system of claim 1, wherein the isomerization compound comprises:

one of octane, heptane, hexane, pentane and butane.

4. The system of claim 1, wherein the isomerization compound comprises:

2,2-dimethylbutane.

5. The system of claim 1, wherein an output of the shell and tube catalytic heat exchanger is in fluid communication with an engine to provide an endothermically isomerized isomerization compound to the engine as fuel.

6. A system for rejecting heat from equipment using endothermic isomerization, comprising:

heat-generating equipment situated on-board an aircraft;

a heat exchanger configured to receive a liquid process fluid and an isomerization compound capable of endothermic isomerization, wherein the liquid process fluid circulates between the heat-generating equipment and the heat exchanger;

a pump for urging the isomerization compound into the heat exchanger; and a heat sink controller for controlling the pump;

wherein, when the system is in operation, the liquid process fluid transfers heat to the isomerization compound and the isomerization compound endothermically isomerizes to a higher energy state form.

7. A system for rejecting heat from equipment using endothermic isomerization, comprising:

heat-generating equipment situated on-board an aircraft;

a heat exchanger configured to receive a liquid process fluid and an isomerization compound capable of endothermic isomerization, wherein the liquid process fluid circulates between the heat-generating equipment and the heat exchanger;

a valve in fluid communication with an output of the heat exchanger; and a pressure controller for operating the valve to maintain a desired pressure in the heat exchanger;

wherein, when the system is in operation, the liquid process fluid transfers heat to the isomerization compound and the isomerization compound endothermically isomerizes to a higher energy state form.

\* \* \* \* \*